United States Patent [19]

Clum et al.

[11] Patent Number: 4,911,932
[45] Date of Patent: Mar. 27, 1990

[54] SKIN CARE COMPOSITIONS

[75] Inventors: Charles E. Clum, Kingston; David M. Isaacson, East Brunswick, both of N.J.

[73] Assignee: Johnson and Johnson Consumer Products, Inc., New Brunswick, N.J.

[21] Appl. No.: 700,165

[22] Filed: Feb. 11, 1985

Related U.S. Application Data

[63] Continuation-in-part of Ser. No. 571,763, Jan. 18, 1984, abandoned.

[51] Int. Cl.$^4$ ............................................. A61K 33/30
[52] U.S. Cl. ..................................................... 424/642
[58] Field of Search ................................. 424/145, 642

[56] References Cited

U.S. PATENT DOCUMENTS 4,122,170 10/1978 Rajadhyaksha ............ 424/DIG. 10
4,161,526 7/1979 Gorman ............................... 424/145
4,318,926 3/1982 Schmidt-Ruppin et al. ....... 424/267

Primary Examiner—Joseph A. Lipovsky
Attorney, Agent, or Firm—Steven P. Berman

[57] ABSTRACT

A skin care composition having improved effectiveness in preventing and treating acute inflammatory skin conditions comprising miconazole nitrate and zinc oxide.

4 Claims, No Drawings

SKIN CARE COMPOSITIONS

CROSS REFERENCE TO RELATED APPLICATIONS

This application is a continuation-in-part of application Ser. No. 571,763, filed Jan. 18, 1984, now abandoned.

BACKGROUND OF THE INVENTION

This invention relates to skin care compositions. More particularly, this invention relates to skin care compositions which can be applied topically to prevent or treat acute inflammatory skin conditions, especially in young children.

One of the most prevalent inflammatory skin conditions to afflict infants and young children is "diaper rash". Diaper rash is an acute, superficial inflammatory dermatitis which is frequent during the diaper wearing period. It is characterized by maceration, chaffing and erythematous papules, and the skin is sensitive and painful to the touch. The sites of inflammation are normally the buttocks, groin, inner thighs and the folds of joints. In severe cases the inflammation is complicated by infection with one or more of the indigeneous saprophytic micro-organisms which are present in the diaper area notably bacteria such as *Staphylococcus aureus* or yeast such as *Candida albicans.*

Over the years numerous methods of prevention and treatment of diaper rash have been advocated with varying degrees of success. Zinc oxide, purified talcs and corn starch have been suggested for use in various formulations to act as protectants and as absorbents of moisture and sweat. Various agents suggested to promote healing have included peruvian balsam, cod liver oil and vitamins A and D as well as various antibiotics, antifungal agents and quaternary ammonium chloride compounds.

Notwithstanding the long term use and acceptance of some of the above agents and the varying degrees of success achieved with them, there is an ongoing need and search for more effective compositions and agents for the prevention and treatment of diaper rash.

SUMMARY OF THE INVENTION

It is an object of this invention to provide improved skin care compositions.

It is another object of this invention to provide improved skin care compositions for the prevention and treatment of diaper rash.

Other objects of this invention will be set forth in, or be apparent from, the following detailed description of the invention.

The foregoing objects and other features and advantages of the present invention are achieved by skin care compositions comprising a synergistic combination of active ingredients which effectively prevent and/or treat inflammatory skin conditions such as diaper rash. More specifically, the present invention relates to skin care compositions comprising a synergistic mixture of a specific imidazole derivative and zinc oxide.

DETAILED DESCRIPTION OF THE INVENTION

In general, this invention comprises a synergistic combination of a specific imidazole derivative and zinc oxide. The term "synergistic combination" as used herein refers to a mixture of two discrete compounds which display a degree of total activity which is greater than the average of the sum of the activity of the compounds taken individually.

The specific imidazole derivative which has been found useful in the present invention is miconazole nitrate of the formula.

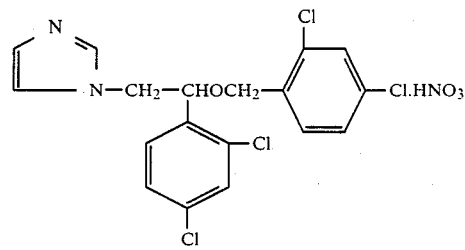

This compound can also be designated as 1-[2-(2,4-dichlorophenyl)-2-[(2,4-dichlorophenyl)methoxy]ethyl]-1H-imidazole, mono nitrate.

This compound and a method of preparation are more fully described in U.S. Pat. No. 3,717,655, which is incorporated herein by reference. These compounds can be prepared by preparing a suspension of α-(2,4-dichlorophenyl)-imadazole-1-ethanol and sodium hydride in dry tetrahydrofuran. This suspension is stirred and refluxed for two hours and after this reaction time, the evolution of hydrogen is ceased. Then there are added successively dimethylformamide and 2,4-dichlorobenzylchloride and stirring and refluxing is continued for an additional two hours. The tetrahydrofuran is removed at atmospheric pressure and the dimethylformamide solution is poured into water. The product is extracted with benzene, washed with water, dried, filtered and evaporated in vacuo. From the residual oily-free base, the nitrate is prepared in the usual manner in 2-propanol by treatment with concentrated nitric acid, yielding, after recrystallization, the miconazole nitrate.

The other compound in the synergistic combination is a pharmaceutical grade of zinc oxide which is readily available from a number of commercial sources.

The ratio of the miconazole nitrate to zinc oxide in the synergistic combinations of this invention can vary from about 1:40 to 1:1900, preferably from about 1:60 to 1:1900. A most preferred embodiment would have a ratio of miconazole nitrate to zinc oxide of about 1:60.

Although the synergistic combinations of the invention may be used in various compositions, they are particularly useful in skin care compositions in an ointment, cream or lotion form. In such compositions they are combined with known ingredients normally utilized in such compositions including but not limited to carriers and vehicles, lubricants, emollients, emulsifiers, thickeners, powders, coloring, perfumes and the like.

The synergistic combinations of the present invention may be incorporated into various compositions separately or they may first be premixed and then added. They may be added in either aqueous or oleaginous media. It is customary but not essential to mill or homogenize the compositions containing the synergistic combinations to ensure uniformity and smooth, non-gritty dispersions. Frequently, a thickener or stabilizer is added to prevent settling of the synergistic combinations and the resulting non-uniformity of the finished product upon standing. Combinations containing about 0.25% miconazole nitrate and 15.0% zinc oxide have been demonstrated to be synergistic and particularly effective. It is fully expected that combinations containing higher concentrations of the components and ratios greater than 1:60, miconazole nitrate to zinc oxide, would also be synergistic and effective even though such concentrations and ratios are presently believed to be therapeutically unnecessary.

Specific embodiments of the compositions prepared in accordance with the present invention are illustrated by the following representative examples. It will be understood, however, that the invention is not confined to the specific limitations set forth in the individual examples, but rather to the scope of the appended claims.

EXAMPLE I

A cream skin care composition is prepared by adding into a suitable container 36.74 g. mineral oil, 5.5 g. anhydrous lanolin, 8.0 g. white wax, 4.57 g. paraffin hard wax, 7.0 g. synthetic beeswax, 1.0 g. glyceryl monostearate, 6.85 g. ceresine wax, and 15.0 zinc oxide. The mixture is heated to 70° C. and stirred until uniform and then added with vigorous stirring to a mixture of 0.9 g. borax, 0.25 g. miconazole nitrate, 0.1 g. propylparaben and 13.93 g. deionized water at 70° C. The resulting emulsion is cooled to 50° C. and 0.16 g. fragrance is added and the emulsion is cooled to 40° C. and placed in suitable containers.

The resulting composition has the following formulation:

|  | % by wt. |
|---|---|
| mineral oil | 36.74 |
| lanolin, anhydrous | 5.50 |
| white wax | 8.00 |
| paraffin hard wax | 4.57 |
| synthetic beeswax | 7.00 |
| glyceryl monostearate | 1.00 |
| ceresine wax | 6.85 |
| zinc oxide | 15.00 |
| borax | 0.90 |
| miconazole nitrate | 0.25 |
| fragrance | 0.16 |
| propylparaben | 0.10 |
| deionized water | qs. to 100 |

EXAMPLE II

An ointment skin care composition is prepared by placing 34.85 g. petrolatum, 3.0 g. polyethylene, 33.8 g. cyclomethicone, 10.0 g. dimethicone, 1.0 g. mineral oil, 2.0 g. silicon dioxide, 0.1 g. propylparaben, 15.0 g. zinc oxide and 0.25 g. miconazole nitrate in a suitable vessel and heating to 60° C. The resulting composition is homogenized and cooled to 35° C. and filled into suitable containers.

This composition has the following formulation:

|  | % by wt. |
|---|---|
| petrolatum | 34.85 |
| polyethylene | 3.00 |
| cyclomethicone | 33.80 |
| dimethicone | 10.00 |
| mineral oil | 1.00 |
| silicon dioxide | 2.00 |
| propylparaben | 0.10 |
| zinc oxide | 15.00 |
| miconazole nitrate | 0.25 |
| | 100.00 |

EXAMPLE III

A lotion skin care composition is prepared by placing in a suitable mixing vessel 69.80 g. deionized water and dispersing therein 0.3 g. Carbopol 934. 4.0 g. propylene glycol are added and the mixture is heated to 80° C. While maintaining the temperature at 80° C., 1.0 g. of isopropyl palmitate, 1.25 g. oleic acid, 0.8 g. sorbitan stearate, 0.5 g. cetyl alcohol, 0.5 g. stearyl alcohol, 0.5 g. synthetic beeswax, 1.25 g. glyceryl stearate, 1.25 g. stearic acid, 1.2 g. Polysorbate 61 and 1.5 g. myristyl myristate are added. This is followed by the addition of 0.13 g. sodium hydroxide, 0.05 g. butylparaben, 0.1 g. propylparaben, 0.15 g. methylparaben and 0.02 g. butylated hydroxytoluene. The resulting emulsion is cooled to 50° C. and 0.3 g. benzyl alcohol, 15.0 g. zinc oxide, 0.25 g. miconazole nitrate and 0.15 g. fragrance and coloring are added. The resulting composition is homogenized and cooled to room temperature.

This composition has the following formulation:

|  | % by wt. |
|---|---|
| Carbopol 934 (B. F. Goodrich's tradename for a polymer of acrylic acid cross-linked with a polyfunctional agent) | 0.30 |
| propylene glycol | 4.00 |
| isopropyl palmitate | 1.00 |
| oleic acid | 1.25 |
| sorbitan stearate | 0.80 |
| cetyl alcohol | 0.50 |
| stearyl alcohol | 0.50 |
| synthetic beeswax | 0.50 |
| glyceryl stearate | 1.25 |
| stearic acid | 1.25 |
| Polysorbate 61 (polyoxyethylene (21) sorbitan mono-oleate) | 1.20 |
| myristyl myristate | 1.50 |
| sodium hydroxide | 0.13 |
| butylparaben | 0.05 |
| propylparaben | 0.10 |
| methylparaben | 0.15 |
| butylated hydroxytoluene | 0.02 |
| benzyl alcohol | 0.30 |
| zinc oxide | 15.00 |
| miconazole nitrate | 0.25 |
| fragrance and coloring | 0.15 |
| deionized water | q.s. to 100 |

EXAMPLE IV

An ointment skin care composition is prepared in accordance with the procedure of Example II and has the following formulation:

|  | % by w/w |
|---|---|
| white petrolatum | 84.75 |
| zinc oxide | 15.00 |
| miconazole nitrate | 0.25 |
|  | 100.00 |

EXAMPLE V

An ointment skin care composition is prepared in accordance with the procedure of Example II and has the following formulation:

|  | % wt/wt |
| --- | --- |
| white petrolatum | 81.35 |
| zinc oxide | 15.00 |
| Thixcin R (NL Chemical's tradename for trihydroxystearin) | 3.00 |
| miconazole nitrate | 0.25 |
| fragrance | 0.40 |
|  | 100.00 |

EXAMPLE VI

The synergistic efficacy of the combinations of the present invention can be established by the following in-vivo test procedure: utilizing zinc oxide and miconazole nitrate in a base consisting of petrolatum and a biologically inert thickener. In this test the base containing 15% zinc oxide, the base containing 0.25% miconazole nitrate and the base containing both 0.25% miconazole nitrate and 15% zinc oxide are compared using the following procedure.

Twenty microliters of a saline suspension of *C. albicans* containing 1 million cells per milliliter are applied to three one square centimeter test sites on the volar forearm surface of each volunteer subject. The areas are covered with an impermeable plastic film and secured with tape. The test sites are uncovered six hours after inoculation and treated with one of the test products or left untreated as a control. The sites are then redressed with plastic film for an additional 24 hours. The test products are then removed from all sites and cultures are obtained by a standard detergent scrub method. Clinical measuremehts are obtained for each site immediately prior to treatment, at 24 hours and at 48 hours after treatment. Grading is done on a scale of 0=no reaction, 1=minute pinpoint papules and/or faint erythema, 2=at least 5 discrete papules or pustules and definite erythema, 3=greater than 10 papules or pustules and erythema, 4=confluent papules or pustules and intense erythema.

The results show a statistically significant synergistic effect for the base containing the combination of miconazole nitrate and zinc oxide at a ratio of about 1:60 compared to the sum of the bases each containing only one of the components.

EXAMPLE VII

A quantitative technique can be used to determine the synergistic effect of zinc oxide on the ability of miconazole nitrate to inhibit the growth of *Staphylococcus aureus* and *Candida albicans*. This technique consists of preparing weighed suspensions of zinc oxide and/or miconazole nitrate in measured volumes of melted microbial growth supporting agars. Aliquots of these agar suspensions are transferred to petri plates and allowed to solidify. During the solidifying process, the zinc oxide and/or miconazole nitrate particles are maintained in suspension in the agar in the petri plates by imparting constant motion to the plates positioned on a reciprocating or rotary platform shaker. To the surface of the solidified agar suspension is added 0.02-0.1 ml of inoculum of *C. albicans* or of *S. aureus* containing approximately 300 colony forming units (CFU)/volume of microbial suspension added ($1.5 \times 10^4 - 3 \times 10^3$ CFU/ml, respectively). The organisms are then distributed evenly over the agar surface with a sterile glass spreader.

The *S. aureus* plates are incubated 2 to 4 days at 35° C. and the *C. albicans* plates are incubated 5 to 7 days at 25° C. After the incubation period, the plates are examined for evidence of growth inhibition by determining the presence or absence of surface colonies. The number of colonies on each plate at each concentration of miconazole nitrate alone is noted. Similarly the number of colonies is noted on each plate at each concentration of zinc oxide alone, and on plates containing combinations of different concentrations of both miconazole nitrate and zinc oxide.

The "percent inhibition" of the bacteria or of the yeast produced at ony one concentration of miconazole nitrate alone is calculated by comparing the number of colonies obtained at that concentration with the number of colonies of the negative control plate containing no zinc oxide or miconazole nitrate. Similarly, the "percent inhibition" produced at one concentration of zinc oxide alone is calculated by comparing the number of colonies obtained at that concentration of zinc oxide with the number of colonies produced on the negative control plates containing no miconazole nitrate or zinc oxide.

To determine the effect of zinc oxide on miconazole nitrate activity, the "percent inhibition" of the organisms in contact with any of the combinations of zinc oxide and miconazole nitrate concentrations are calculated by relating the number of surviving colonies on the agar surface of those plates with the number of surviving colonies on the base line control plates containing the same concentration of zinc oxide alone. When the zinc oxide and miconazole nitrate combinations are tested according to the above procedures, the following examples of the results are obtained. These results are expressed as percent inhibition of the organism at a specific concentration of miconazole nitrate alone (Inhibition for Miconazole); as percent inhibition of the organism at a specific concentration of zinc oxide alone (Inhibition for Zinc Oxide); as the percent inhibition expected if the inhibition obtained for miconazole nitrate and for zinc oxide were additive (Sum of Components), and as the observed inhibition at specific concentrations of zinc oxide and miconazole nitrate (Inhibition for Combination). After observation of a repeated 100.0% inhibition, no further ratios are tested at the stated concentrations of miconazole nitrate and zinc oxide.

TABLE I

Synergistic Activity of Zinc Oxide on Miconazole Nitrate Inhibition of the Growth of *Staphylococcus aureus* at Miconazole Nitrate Concentration of $0.75 \times 10^{-4}$ % W/V

| Zinc Oxide Concentration $\times 10^{-2}$ % W/V | Inhibition for Miconazole Nitrate | Inhibition for Zinc Oxide | Sum of Components | Inhibition for Combination |
| --- | --- | --- | --- | --- |
| 0.00 | 14.6 | 0.0 | 14.6 | 14.6 |
| 0.21 | 14.6 | 7.0 | 21.6 | 17.4 |
| 0.42 | 14.6 | 15.1 | 29.7 | 29.7 |
| 0.83 | 14.6 | 40.2 | 54.8 | 100.0 |
| 1.67 | 14.6 | 56.9 | 71.5 | 100.0 |
| 2.50 | 14.6 | 78.9 | 93.5 | 100.0 |

These results exhibit synergism at ratios of from about 1:110 to 1:333, miconazole nitrate to zinc oxide. If ratios above 1.333 were to be tested at the same concentrations, 100.0% inhibition would be observed.

TABLE II

Synergistic Activity of Zinc Oxide on Miconazole Nitrate Inhibition of the Growth of *Staphylococcus aureus* at Miconazole Nitrate Concentration of $0.75 \times 10^{-4}\%$ W/V

TABLE II

Synergistic Activity of Zinc Oxide on Miconazole Nitrate Inhibition of the Growth of *Staphylococcus aureus* at Miconazole Nitrate Concentration of $0.75 \times 10^{-4}\%$ W/V

| Zinc Oxide Concentration × $10^{-2}\%$ W/V | Inhibition for Miconazole Nitrate | Inhibition for Zinc Oxide | Sum of Components | Inhibition for Combination |
|---|---|---|---|---|
| 0.00 | 21.1 | 0.0 | 21.1 | 21.1 |
| 0.16 | 21.1 | 11.4 | 32.5 | 13.2 |
| 0.31 | 21.1 | 14.1 | 35.2 | 39.6 |
| 0.63 | 21.1 | 18.2 | 39.3 | 97.7 |
| 1.25 | 21.1 | 38.6 | 59.7 | 100.0 |
| 2.50 | 21.1 | 61.7 | 82.8 | 100.0 |

These results exhibit synergism at ratios of from about 1:40 to 1:333, miconazole nitrate to zinc oxide. If ratios about 1.333 were to be tested at the same concentrations, 100.0% inhibition would be observed.

TABLE III

Synergistic Activity of Zinc Oxide on Miconazole Nitrate Inhibition of the Growth of *Candida albicans* at Miconazole Nitrate Concentration of $3.13 \times 10^{-4}\%$ W/V

TABLE III

Synergistic Activity of Zinc Oxide on Miconazole Nitrate Inhibition of the Growth of *Candida albicans* at Miconazole Nitrate Concentration of $3.13 \times 10^{-4}\%$ W/V

| Zinc Oxide Concentration × $10^{-2}\%$ W/V | Inhibition for Miconazole Nitrate | Inhibition for Zinc Oxide | Sum of Components | Inhibition for Combination |
|---|---|---|---|---|
| 0.00 | 15.4 | 0.0 | 15.4 | 15.4 |
| 3.75 | 15.4 | 2.0 | 17.4 | 16.4 |
| 7.50 | 15.4 | 2.0 | 17.4 | 31.4 |
| 15.00 | 15.4 | 2.0 | 17.4 | 46.3 |
| 30.00 | 15.4 | 2.0 | 17.4 | 100.0 |
| 60.00 | 15.4 | 2.0 | 17.4 | 100.0 |

These results exhibit synergism at ratios of from about 1:240 to 1:1900, miconazole nitrate to zinc oxide.

TABLE IV

Synergistic Activity of Zinc Oxide on Miconazole Nitrate Inhibition of the Growth of Candida albicans at Miconazole Nitrate Concentrations of $3.13 \times 10^{-4}\%$ W/V

TABLE IV

Synergistic Activity of Zinc Oxide on Miconazole Nitrate Inhibition of the Growth of *Candida albicans* at Miconazole Nitrate Concentration of $3.13 \times 10^{-4}\%$ W/V

| Zinc Oxide Concentration × $10^{-2}\%$ W/V | Inhibition for Miconazole Nitrate | Inhibition for Zinc Oxide | Sum of Components | Inhibition for Combination |
|---|---|---|---|---|
| 0.00 | 10.4 | 0.0 | 10.4 | 10.4 |
| 3.75 | 10.4 | 3.0 | 13.4 | 22.2 |
| 7.50 | 10.4 | 3.0 | 13.4 | 41.8 |
| 15.00 | 10.4 | 3.0 | 13.4 | 67.4 |
| 30.00 | 10.4 | 3.0 | 13.4 | 100.0 |
| 60.00 | 10.4 | 3.0 | 13.4 | 100.0 |

These results exhibit synergism at ratios of from about 1:120 to 1:1900, miconazole nitrate to zinc oxide.

Various other features and embodiments of the present invention not specifically set forth herein will be readily obvious to those skilled in the art, all of which may be achieved without departing from the spirit and scope of the invention as defined by the following claims.

What is claimed is:

1. A skin care composition comprising as the active components
   (a) miconazole nitrate of the formula

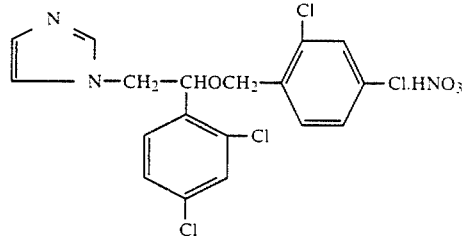

and
   (b) zinc oxide;
wherein the miconazole nitrate and zinc oxide are present in a ratio of from about 1:60 to about 1:333.

2. The composition of claim 1 wherein the miconazole nitrate and zinc oxide are present in a ratio of about 1:60.

3. A method for treating diaper rash comprising applying to the affected skin area a composition containing an antimicrobially effective amount of
   (a) miconazole nitrate of the formula

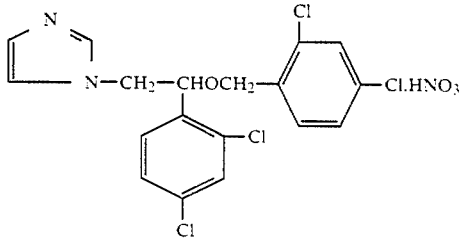

and
   (b) zinc oxide;
wherein the miconazole nitrate and zinc oxide are present in a ratio of from about 1:60 to about 1:333.

4. The method of claim 3 wherein the miconazole nitrate and zinc oxide are present in a ratio of about 1:60.

* * * * *